United States Patent [19]

Fournier et al.

[11] Patent Number: 4,618,459
[45] Date of Patent: * Oct. 21, 1986

[54] SUBSTITUTED 2,4-DIALKOXY BENZENE SULFONYL CHLORIDES

[75] Inventors: Jean-Paul Fournier, Versailles; Patrick Choay, Paris, both of France

[73] Assignee: Choay S.A., Paris, France

[*] Notice: The portion of the term of this patent subsequent to Jul. 3, 2001 has been disclaimed.

[21] Appl. No.: 567,161

[22] Filed: Dec. 30, 1983

Related U.S. Application Data

[63] Continuation of Ser. No. 371,451, Apr. 23, 1982.

[30] Foreign Application Priority Data

Apr. 23, 1981 [FR] France ............................. 81 08126

[51] Int. Cl.$^4$ .................. C07C 143/70; C07C 147/06
[52] U.S. Cl. ................................................ 260/543 R
[58] Field of Search ................................... 260/543 R

[56] References Cited

U.S. PATENT DOCUMENTS 3,453,099  7/1969  Popoff et al. ......................... 71/103
4,457,875  7/1984  Fournier et al. ................ 260/543 R

FOREIGN PATENT DOCUMENTS 2378004  8/1978  France .

OTHER PUBLICATIONS

Dorn, H. W. et al., *J. Am. Chem. Society*, vol. 61, (1939) pp. 141-147.

Bottino, F. et al., *Journal of the Chemical Society*, Perkin I (3/1981) pp. 718-722.

*Primary Examiner*—Natalie Trousof
*Assistant Examiner*—L. Hendriksen
*Attorney, Agent, or Firm*—Weiser & Stapler

[57] ABSTRACT

The invention relates to trisubstituted sulfohalides, the process for their preparation and their use as intermediate products for the manufacture of novel compounds.

The trisubstituted sulfohalides according to the invention correspond to the following general formula (I):

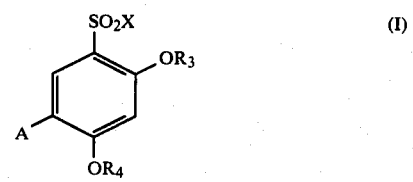

in which:

X is a halogen atom, particularly bromine or preferably chlorine;

$R_3$ and $R_4$ each represent, independently of one another, a lower alkyl radical having from 1 to 4 carbon atoms, A represents hydrogen, halogen, alkoxy radicals having from 1 to 4 carbon atoms, alkylsulfonyl groups having from 1 to 4 carbon atoms, or the group $NO_2$, or $CF_3$.

The invention is useful in the manufacture of medicaments.

10 Claims, No Drawings

SUBSTITUTED 2,4-DIALKOXY BENZENE SULFONYL CHLORIDES

This is a continuation of application Ser. No. 371,451, filed Apr. 23, 1982.

The invention relates to new compounds of the trisubstituted sulfohalide type as well as to the method for preparing the same.

The invention also relates to the application of these new sulfohalides, in particular in the preparation of new compounds of the trisubstituted benzenesulfonamide type particularly useful as the active principles of new mediccaments.

The trisubstituted sulfohalides according to the invention are benzenesulfohalides substituted at the 2, 4, 5, position and corresponding to the following formula:

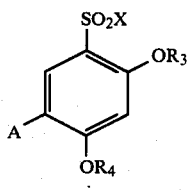

(I)

in which:

X is a halogen atom, particularly bromine or preferably chlorine, $R_3$ and $R_4$ each represent, independently of each other, a lower alkyl radical having from 1 to 4 carbon atoms.

A represents $NO_2$, $CF_3$ a halogen, the alkoxy radicals having from 1 to 4 carbon atoms, the alkylsulfonyl groups having from 1 to 4 carbon atoms.

A preferred class of sulfohalides according to the invention is constituted by 2,4 dialkoxy benzenesulfochlorides substituted at the 5 position and corresponding to the following formula (II):

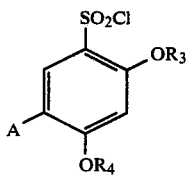

(II)

in which A, $R_3$ and $R_4$ have the above-indicated meanings.

A preferred class of sulfohalides according to the invention, is constituted by 2,4 dimethoxy benzenesulfohalides substituted at the 5 position and corresponding to the formula:

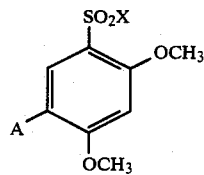

(III)

in which A and X have the above-indicated meanings.

A preferred class of trisubstituted benzenesulfochlorides according to the invention is constituted by sulfochlorides of the following formula (IV):

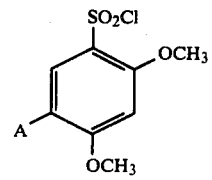

(IV)

in which A has the above-indicated meaning.

Another preferred class of sulfochlorides according to the invention is constituted by those of formula (IV) in which A represents advantageously one of the following radicals: Cl, Br, $OCH_3$, $SO_2CH_3$, $SO_2C_2H_5$, $SO_2nC_3H_7$, $SO_2iC_3H_7$, preferably, Cl, Br, $OCH_3$.

To prepare the sulfohalides of formula (I):

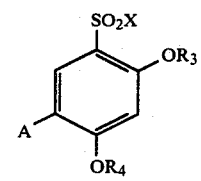

(I)

in which X, A, $R_3$ and $R_4$ have the aboveindicated meanings, recourse may be had to the arylamine of the formula (V):

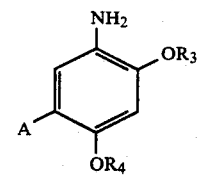

(V)

in which A, $R_4$ and $R_5$ have the aboveindicated meanings, and from which:

(a) the diazonium salt is formed, particularly the diazonium chloride of formula (VI). This diazonium salt is obtained particularly by reacting the arylamine in a solution of the corresponding halogenated acid, especially hydrochloric acid, with a solution of an alkali metal nitrite, and by keeping the reaction mixture at a temperature preferably lower than about 10° C.:

(b) then the diazonium salt thus obtained is reacted in solution with sulfurous anhydride. The operation is preferably carried out in the presence of acetic acid, as well as in the presence of a catalyst suited to assist the conversion of the diazonium group into a sulfohalide group, particularly a sulfochloride. This catalyst is, for example based on copper (modified Sandmeyer reaction).

The steps (a) and (b) of this reaction (applied to the production of trisubstituted sulfochlorides of formula (II) may be represented as follows:

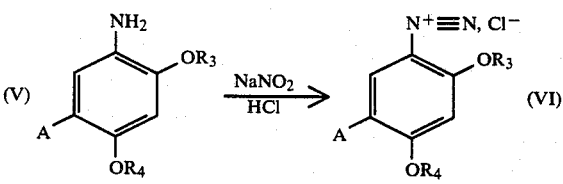

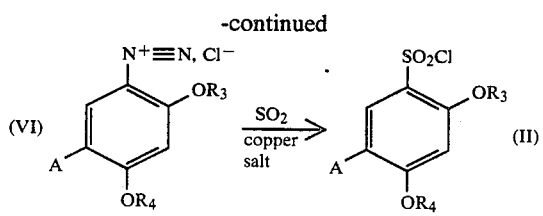

This reaction diagram also applies to the preparation of sulfohalides of formula (I).

The following arylamines may be mentioned as preferred arylamines for the preparation of sulfochlorides of formula (II):
5-chloro 2,4-dimethoxyaniline
5-bromo 2,4-dimethoxyaniline
2,4,5-trimethoxyaniline
2,4-dimethoxy 5-methylsulfonylaniline
2,4 dimethoxy 5-ethylsulfonylaniline
2,4-dimethoxy 5-propylsulfonyl aniline
2,4-dimethoxy 5-isopropylsulfonylaniline To prepare the sulfohalides of formula (I), particularly the sulfochlorides of formula (II), in which A, $R_3$ and $R_4$ have the aboveindicated meaning, it is also possible to proceed by sulfonation or halogenosulfonation, preferably chlorosulfonation of the compound of formula (VII) in which A, $R_3$ and $R_4$ have the aboveindicated meanings:

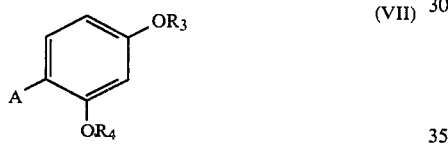

In the case of sulfonation—by reaction of the compound (VII)—with sulfuric acid, in a first stage, the sulfonic acid of formula (VIII) is obtained:

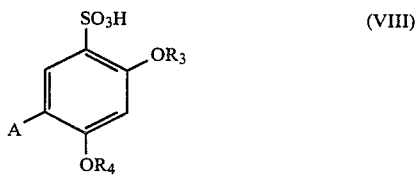

The acid of formula (VIII) obtained can then be converted into a salt of an organic or inorganic base by the action of the appropriate base such as sodium hydroxide, potassium hydroxide or pyridine.

The salt is represented by the following formula (IX):

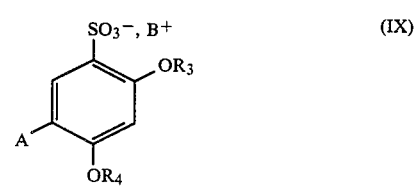

in which $B^+$ represents a metal, particularly an alkali or alkali earth metal, and A has any one of the aboveindicated meanings. The halide of formula (I) and particularly the chloride of formula (II) is then obtained by the action on the compound of formula (VIII) or on an organic or inorganic salt corresponding to formula (IX) of a halogenating agent, particularly chlorinating, such as thionyl chloride, phosphorus pentachloride or phosphorus oxychloride.

By way of example, the reaction diagram for the production of compounds of formula (II) in which A, $R_3$ and $R_4$ has any one of the aboveindicated meanings, from compounds of formula (VII) may be represented as follows:

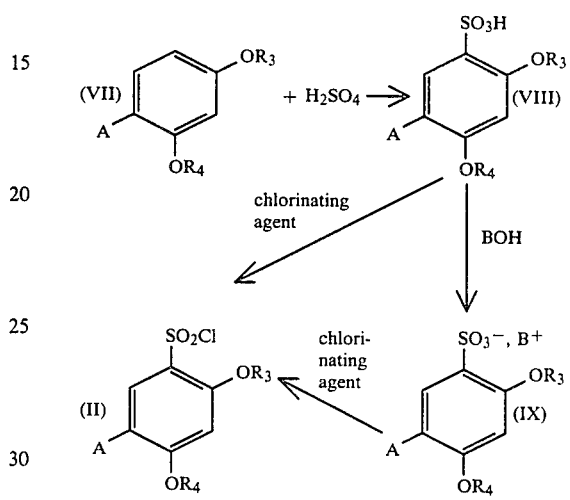

This reaction diagram applies also to the preparation of sulfohalides of formula (I).

In the case of halogenosulfonation, particularly chlorosulfonation, the halogenosulfonic acid, particularly chlorosulfonic acid is reacted with the compound of formula (VII) in which A, $R_3$ and $R_4$ have the aboveindicated meanings.

The reaction applied by way of example, to the preparation of sulfochlorides of formula (II) may be written:

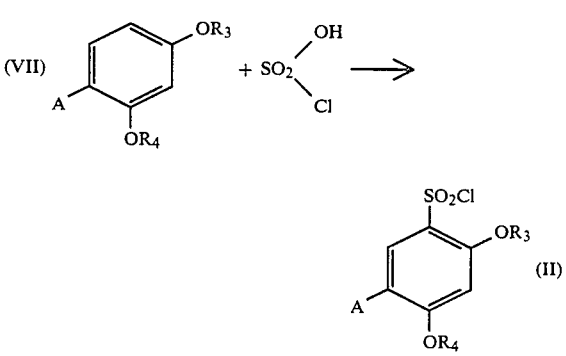

This reaction diagram also applies to the preparation of sulfohalides of formula (I).

The new sulfohalides according to the invention, and more particularly the new sulfochlorides, are useful particularly as intermediate products for the preparation of new 2,4 dialkoxy benzenesulfonamides substituted at the 5 position of formula (X):

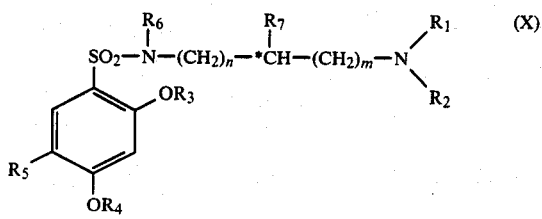

in which:

n and m independently from each other have values from 0 to 4; $R_1$ and $R_2$ represent independently from each other, hydrogen atoms, linear or branched alkyl groups having from 1 to 4 carbon atoms, or forming conjointly with the nitrogen atom a nitrogenous heterocyclic group with 5 or 6 links, especially a pyrrolidino, morpholino, piperazinyl, pyrrol or piperidino group, substituted or not by linear or branched alkyl radicals having from 1 to 4 carbon atoms;

$R_3$ and $R_4$ have the same meanings as those indicated in the definition of formula (I) that is to say each represents, independently of one another, a lower alkyl radical having from 1 to 4 carbon atoms; $R_5$ has the same meaning as that of A indicated in the definition of formula (I), that is to say represents: a halogen, the $NO_2$, or $CF_3$ group, an alkoxy radical having from 1 to 4 carbon atoms, or an alkylsulfonyl radical having from 1 to 4 carbon atoms and can also represent the $NH_2$ group; $R_6$ and $R_7$ represent independently of one another a hydrogen atom, an alkyl radical of 1 to 6 carbon atoms or a cycloalkyl radical of 3 to 6 carbon atoms.

The new sulfohalides according to the invention, particularly the sulfochlorides, are also useful for the preparation of isomers of the compounds of formula (X), when $R_7$ is different from hydrogen.

The new sulfohalides according to the invention, particularly the sulfochlorides, are also useful for the preparation of the physiologically acceptable salts of compounds of formula (X), obtained with organic or inorganic acids.

A preferred class of new 2,4 dialkoxy benzenesulfonamides substituted at the 5 position prepared from sulfohalides, particularly sulfochlorides according to the invention, is constituted by compounds of the formula:

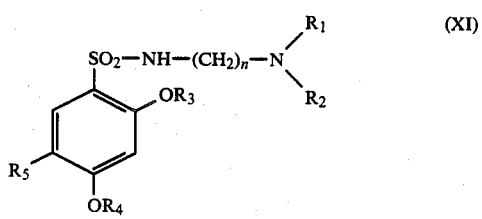

in which n, $R_1$, $R_2$, $R_3$, $R_4$ and $R_5$ have the aboveindicated meanings.

A preferred class of new 2,4 dialkoxy benzenesulfonamides substituted at the 5 position prepared from sulfohalides, particularly sulfochlorides according to the invention, is constituted by the compounds of formula:

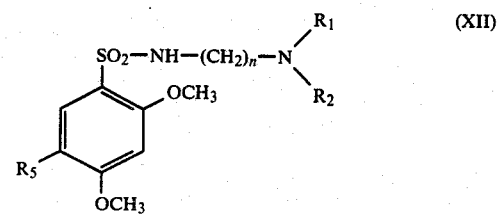

in which n, $R_1$, $R_2$ and $R_5$ have the aboveindicated meanings.

A preferred class of new 2,4 dialkoxy benzenesulfonamides substituted in the 5 position prepared from sulfohalides, particularly sulfochlorides according to the invention, is constituted by the compounds of the formula (XII) in which $R_5$ represents $SO_2CH_3$, $SO_2C_2H_5$, $SO_2nC_3H_7$, $SO_2iC_3H_7$, and preferably Cl, Br, or $OCH_3$.

The compounds of these various 2,4 dialkoxy benzenesulfonamides are advantageously in the form of salts, particularly the hydrochloride.

To prepare the hydrochloride of these new 2,4 dialkoxy benzenesulfonamides substituted at the 5 position an amine of the formula:

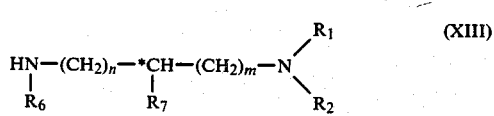

in which n, m, $R_1$, $R_2$, $R_6$ and $R_7$ have the aboveindicated meanings can be reacted with the sulfochloride according to the invention, of formula (II):

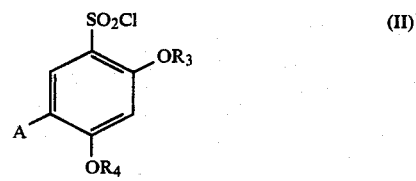

in which $R_3$ and $R_4$ have the aboveindicated meanings and A has any one of the aboveindicated meanings for $R_5$ with the exception of the $NH_2$ group (it being understood that another halogenate of the compounds of formula (X) will be obtained if another sulfohalide is applied, for example a sulfobromide, instead and in place of the abovesaid sulfochloride).

The production of the compounds of formula (X) in which $R_5$ is $NH_2$, is effected by reducing the compound of formula (X) in which $R_5$ is $NO_2$ by catalytic hydrogenation or by chemical reduction.

In this way hydrochlorides of the following formula are obtained:

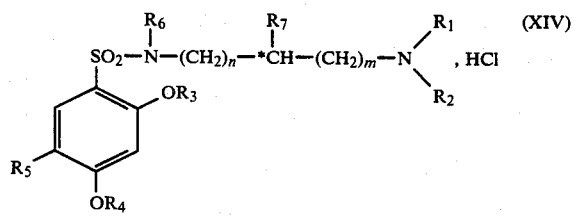

Passage from the hydrochloride of formula (XIV) to the compound of formula (X), unsalified, that is to say in the form of the base, can be done in solution, by reaction with a strong base such as sodium or potassium hydroxide, or any other base having equivalent properties.

The conversion of the hydrochloride of formula (XIV) into a different salt can be done by passing through the base of formula (X), then by forming a salt of the latter according to conventional methods.

A preferred group of amines used in the preparation of the compounds of formula (X) or of their corresponding salts, is constituted by the following:

dimethylamino-ethylamine, diethylamino-ethylamine, pyrrolidino-ethylamine, piperidino-ethylamine, morpholino-ethylamine, dimethylamino-propylamine, diethylamino-propylamine, piperidino-propylamine, 3-(2-methyl piperidino)propylamine, morpholino-propylamine.

The following examples relate to the preparation of a certain number of sulfochlorides and of new 2,4-dialkoxy benzenesulfonamides substituted at the 5 position which serve to illustrate the invention, but which are not limiting.

EXAMPLE 1

Preparation of 2,4,5-trimethoxy benzenesulfonyl chloride

This may be carried out according to two methods:

1st method

Into a triple-necked flask of 500 cm$^3$, provided with a thermometer, with a dropping funnel, with a calcium chloride trap and a magnetic stirring system, were placed 42 g (0.25 mole) of 1,2,4-trimethoxy benzene in solution in 200 cm$^3$ of pure chloroform. The reaction medium, placed under a nitrogen atmosphere and cooled to $-10°$ C., were added drop by drop 80 cm$^3$ of chlorosulfonic acid. Successively a creamy white milky precipitate was formed, then a greenish solution with changes to brown. When the addition was ended, the reaction medium was left to stand 1 h at ambient temperature, then poured over crushed ice. The precipitate obtained was extracted with chloroform; the organic phase was then dried over sodium sulfate and then evaporated under reduced pressure. The brown residue formed was washed with a minimum of toluene until the obtaining of a beige solid which was then chromatographed on a silica column.

Elution with benzene, then with a benzene-chloroform mixture (50-50) gave the 2,4,5-trimethoxy benzenesulfonyl chloride.

Yield 26% mp 147° C.

NMR (CDCl$_3$) at 80 MHz: $\delta$ 7.29 ppm (s 1H ArH); $\delta$ 6.55 ppm (s 1H ArH); $\delta$ 3.93, 3.78 and 3.53 ppm (3s 9H OCH$_3$)

IR (KBr) $\upsilon$ SO$_2$, as 1350 cm$^{-1}$, s 1160 cm$^{-1}$.

2nd method

It comprises 4 steps:

3,4-dimethoxy chlorobenzene:

Into a triple-necked flask of a liter, provided with a magnetic stirring system, with a thermometer, with a calcium chloride trap and with a dropping funnel, were introduced in the cold at about 0° C. and successively 138 g (1 mole) of veratrol then drop by drop 135 g (1 mole) of sulfuryl chloride. When the addition was terminated, the reaction medium was brought to room temperature, then after standing one hour was distilled under reduced pressure.

Yield 83% b.p.: 120° C. under 1 999,83 Pa (15 mm Hg)

4,5-dimethoxy 2-nitro chlorobenzene:

Into a triple-necked flask of one liter, provided with a magnetic stirring system, with a thermometer and a dropping funnel, were introduced successively 143.9 g (0.83 mole) of 3,4-dimethoxy chlorobenzene, then drop by drop 166 cm$^3$ of nitric acid (d=1.38), without the temperature exceeding 25° C. When the addition was ended, the reaction mixture was allowed to stand 1.5 h and then filtered.

Yield 95% mp 105° C.

2,4,5-trimethoxy nitrobenzene:

Into a two liter flask, provided with a cooling device, were introduced successively a solution of methanolic potash (100 g of KOH and 500 cm$^3$ of methanol), then 100 g (0.46 mole) of 4,5-dimethoxy 2-nitro chlorobenzene and carborundum. The mixture was brought to boiling under reflux for 6 h. After cooling, the reaction medium was filtered; the precipitate obtained was washed with methanol.

Yield 95% mp 129° C.

2,4,5-trimethoxy aniline:

Into a 500 cm$^3$ flask, provided with a cooling device, were added successively 21.3 g (0.1 mole) of 2,4,5-trimethoxy nitrobenzene, 80 g of chemically pure stannous chloride for mirror making, 100 cm$^3$ of a hydrochloric acid solution (d=1.18) and carborundum. The mixture was brought to boiling under reflux for 1 h. After cooling, a caustic soda solution was added until the precipitate dissolved. The solution obtained was extracted with methylene chloride. The organic extracts were dried over sodium sulfate then evaporated under reduced pressure. The residue obtained was crystallized in ethanol.

Yield 80% mp 94° C.

2,4,5-trimethoxy benzenesulfonyl chloride:

Into a triple-necked flask of 250 cm$^3$, provided with a stirring system and a thermometer, were introduced 18.3 g (0.1 mole of 2,4,5-trimethoxy aniline then 50 cm$^3$ of a hydrochloric acid solution (d=1.18). After standing for 4 hours, the amine was diazotized at $-5°$ C. by the addition of a sodium nitrite solution (10 g of NaNO$_2$ in 50 cm$^3$ of water). The diazonium salt obtained was poured slowly into a triple-necked flask, heated to 40° C. and under a nitrogen atmosphere, containing 200 cm$^3$ of acetic acid saturated with sulfur dioxide and 7 g of cupric chloride. The mixture was brought for 2 h to 60° C., then poured on to crushed ice.

Yield 35% mp 147° C.

EXAMPLE 2

Preparation of 5-chloro 2,4-dimethoxy benzenesulfonyl chloride

It was carried out in 2 steps from 1,3-dimethoxy benzene:

1st step: Preparation of 2,4-dimethoxy chlorobenzene

Procedure was according to the technique of G. Castelfranchi and G. Borra reported in Annali di Chimica, 1953, 43, 293.

Into a triple-necked flask of 500 cm$^3$, provided with a magnetic stirring system, with a thermometer, with a calcium chloride trap and a dropping funnel, and cooled to 10° C., were introduced successively 97.5 (0.70 mole) of 1,3-dimethoxy benzene and then drop by drop 96.5 g (0.70 mole) of sulfuryl chloride. Once the addition was ended, the solution was brought back to ambient temperature and allowed to stand 2 h and then distilled.

Yield 85% b.p. 137° C. under 2 399,80 Pa (18 mm Hg).

2nd step: Conversion to 5-chloro 2,4-dimethoxy benzenesulfonyl chloride

Into a triple-necked flask of 500 cm³, provided with a magnetic stirring system, with a calcium chloride trap, a thermometer and a dropping funnel, were introduced 35 g (0.2 mole) of 2,4-dimethoxy chlorobenzene in solution in 250 cm² of pure chloroform. The solution was cooled to 0° C., then supplemented drop by drop with 50 cm³ (0.75 mole) of chlorosulfonic acid. Once the addition was ended, the reaction medium was brought to ambient temperature, then left to stand 3 h; it was then poured over crushed ice. The mixture obtained was extracted with chloroform. The organic extracts were dried over sodium sulfate then concentrated to crystallization. The solid obtained was recrystallized in an ethyl ether/benzene mixture.

Yield 74% mp 175° C.

NMR (CDCl₃) at 80 MHz: δ 7.87 ppm (S 1H ArH); δ 6.55 ppm (s 1H ArH); δ 4 and 3.96 ppm (2s 6H OCH₃)

IR (KBr): υ SO₂, as 1385 cm⁻¹, s 1170 cm⁻¹.

EXAMPLE 3

Preparation of 5-bromo 2,4-dimethoxy benzenesulfonyl chloride

This was carried out in 2 steps starting from 1,3-dimethoxy benzene:

1st step: Preparation of 2,4-dimethoxy bromobenzene

This was done according to the procedure of S. T. Feng and K. Y. Chiu reported to Hsueh Pao, 1959, 25, 277.

Into a triple-necked flask of 250 cm³, provided with a magnetic stirring system, with a thermometer, and cooled to 10° C., were added successively 27.6 g (0.2 mole) of 1,3-dimethoxy benzene then in small portions 36 g (0.2 mole) of N-bromosuccinimide. Once the addition was ended, the reaction medium was brought to ambient temperature and left to stand 2 h. After washing with water and extraction with chloroform, the organic extracts were dried over sodium sulfate then concentrated under reduced pressure. The residual liquid was distilled.

Yield 82% b.p.: 150° C. under 1 999,83 Pa (15 mm Hg).

2nd step: Conversion to 5-bromo 2,4-dimethoxy benzenesulfonyl chloride

It was obtained according to the same procedure as that described in Example 3 to prepare 5-chloro 2,4-dimethoxy benzenesulfonyl chloride. By using 65.1 g (0.3 mole) of 2,4-dimethoxy bromobenzene and 100 cm³ of chlorosulfonic acid, the yield was 77%.

mp 195° C.

NMR (CDCl₃) at 60 MHz δ 7.85 ppm (s 1H ArH); δ 6.70 ppm (s 1H ArH); δ 3.92 and 3.88 ppm (2s 6H OCH₃);

IR (KBr): υ SO₂, as 1385 cm⁻¹, s 1165 cm⁻¹.

EXAMPLE 4

5-alkylsulfonyl 2,4-dimethoxy benzenesulfonyl chlorides

They were obtained from the 2,4-dimethoxy benzenesulfonyl chlorides described in Example 1. The general diagram for their preparation is as follows:

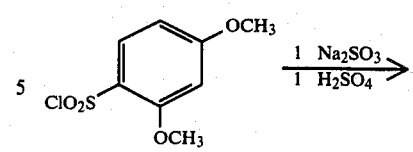

2,4-dimethoxy benzenesulfonyl chloride

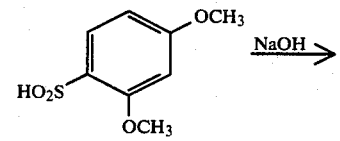

2,4-dimethoxy benezenesulfinic acid

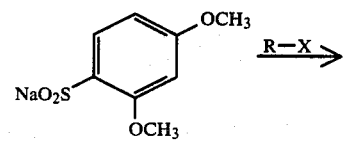

Sodium 2,4-dimethoxy benzenesulfinate

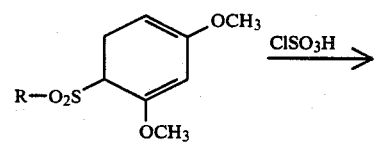

(2,4-dimethoxy phenyl) alkylsulfone

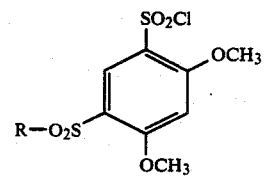

5-alkylsulfonyl 2,4-dimethoxy benezenesulfonyl chloride 2,4-dimethoxy benzenesulfinic acid To an aqueous solution containing 129 g (0.974 mole) of sodium sulfite were added in small amounts and with stirring 115 g (0.487 mole) of 2,4-dimethoxy benzenesulfonyl chloride. During this operation, the pH was kept alkaline by the addition of caustic soda. After standing for 3 h, the reaction medium was filtered. The filtrate was acidified with 2N sulfuric acid until the precipitation of the sulfinic acid.

Yield 72% mp 122° C.

Sodium 2,4-dimethoxy benzenesulfinate

This was obtained by the addition of the stoichiometric amount of sodium hydroxide in aqueous solution. The sulfinate solution was evaporated to dryness.

(2,4-dimethoxy phenyl)alkylsulfones

General procedure:

Into a 500 cm³ flask, provided with a cooling system and a magnetic stirring system, were added successively 0.1 mole of sodium 2,4-dimethoxy benzenesulfonate, 250 cm³ of isopropanol, and then 0.15 mole of alkyl halide, preferably an iodide. The mixture was brought to boiling under reflux 5 to 30 h according to the halide used. After cooling, the reaction medium was evaporated tu dryness. The residue was taken up again in water and then extracted with chloroform. The evaporation of the organic phase, after drying over sodium sulfate gave an oil which was crystallized in benzene.

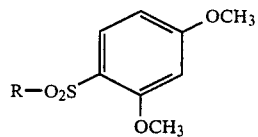

| R | MW | Time of heating | MP °C. | Yield % |
|---|---|---|---|---|
| CH₃ | 216 | 5 h | 109 | 65 |
| C₂H₅ | 230 | 7 h | 94 | 70 |
| nC₃H₇ | 244 | 15 h | 70 | 90 |
| iC₃H₇ | 244 | 30 h | 100 | 64 |

5-alkylsulfonyl 2,4-dimethoxy benzenesulfonyl chlorides

General procedure:

Into a triple-necked flask of one liter, provided with a magnetic stirring system, with a calcium chloride trap, with a thermometer and a dropping funnel, was introduced a solution of (2,4-dimethoxy-phenyl)alkylsulfone (0.2 mole) in 200 cm³ of pure chloroform. After cooling to −10° C., 100 cm³ of chlorosulfonic acid were added drop by drop. Once the addition was ended, the mixture was left to stand 0.5 h at −10° C., then brought back to room temperature and left with stirring for 7 h; it was then poured over crushed ice. The mixture obtained was extracted with chloroform. The organic phase was dried over sodium sulfate, filtered, then evaporated under reduced pressure. The residue was crystallized in benzene.

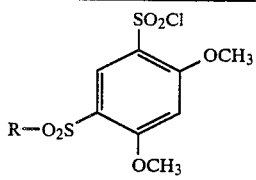

| R | MW | MP °C. | Yield % |
|---|---|---|---|
| CH₃ | 314,5 | 204 | 52 |
| C₂H₅ | 328,5 | 191 | 77 |
| nC₃H₇ | 342,5 | 169 | 87 |
| iC₃H₇ | 342,5 | 218 | 66 |

2,4-dimethoxy 5-methylsulfonyl benzenesulfonyl chloride

NMR (DMSO) at 80 MHz: δ 8.2 ppm (s 1H ArH); δ 6.9 ppm (s 1H ArH); δ 4.1 ppm and 4.05 ppm (2s 6H OCH₃); 3.2 ppm (s 3H CH₃).

IR (KBr): υ SO₂—Cl, as 1360 cm⁻¹, s 1170 cm⁻¹; υ SO₂—CH₃, as 1300 cm⁻¹, s 1140 cm⁻¹;

5-ethylsulfonyl 2,4-dimethoxy benzenesulfonyl chloride

NMR (DMSO) at 80 MHz: δ 8.2 ppm (s 1H ArH); δ 6.93 ppm (s 1H ArH); δ 4.15 ppm and 4.1 ppm (2s 6H OCH₃); δ 3.25 ppm (q 2H —CH₂—); δ 1.18 ppm (t 3H CH₃—).

IR (KBr): υ SO₂—Cl, as 1370 cm⁻¹, s 1175 cm⁻¹; υ SO₂—CH₂—, as 1315 cm⁻¹, s 1140 cm⁻¹.

2,4-dimethoxy 5-propylsulfonyl benzenesulfonyl chloride

NMR (DMSO) at 80 MHz: δ 8.05 ppm (s 1H ArH); δ 6.72 ppm (s 1H ArH); 3.92 and 3.87 ppm (2s 6H OCH₃); δ 3.2 ppm (t 2H—CH₂—SO₂—); δ 1.45 ppm (m 2H—CH₂—); δ 0.85 ppm (t 3H CH₃).

IR (KBr): υ SO₂Cl, as 1370 cm⁻¹, s 1180 cm⁻¹; υ SO₂—CH₂, as 1315 cm⁻¹, s 1135 cm⁻¹.

5-isopropylsulfonyl 2,4-dimethoxy benzenesulfonyl chloride

NMR (DMSO) at 80 MHz: δ 8.02 ppm (s 1H ArH); δ 6.7 ppm (s 1H ArH); δ 3.92 and 3.85 ppm (2s 6H OCH₃); δ 3.48 ppm (m 1H

δ 1.11 and 1.03 ppm (2s 6H CH₃).

IR (KBr): υ SO₂—Cl, as 1365 cm⁻¹, s 1175 cm⁻¹; υ SO₂—CH, as 1300 cm⁻¹, s 1130 cm⁻¹.

EXAMPLE 5

Preparation of N-substituted 2,4-dimethoxy benzenesulfonamides

To 0.015 mole of benzenesulfonyl chloride in solution in a mixture of methylene chloride (40 cm³) and methanol (10 cm³), was added 0.015 mole of dialkylaminoalkylamine in solution in 10 cm³ of methylene chloride. After standing 2 h, with stirring and at room temperature, the reaction medium was evaporated to dryness and then taken up again in 50 cm³ of water. The aqueous solution was washed with ethyl ether, then evaporated to dryness. The residue was crystallized in an isopropanol/methanol mixture. Possible conversion to the base was carried out by treating the aqueous solution of the hydrochloride with N soda until precipitation. The precipitate was extracted with methylene chloride. The organic solution was dried then evaporated under reduced pressure. The base obtained was crystallized in an ethyl ether/petroleum ether mixture.

Other compounds were prepared similarly and are assembled in the following Table I (the melting point indicated for each compound is, except for indication to the contrary, that of the hydrochloride).

TABLE I
COMPOUNDS OF FORMULA

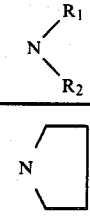

| Product n° | NR₁R₂ | n | R₅ | Formula of compound in form of hydrochloride | Molecular weight | Melting point of hydrochloride | Yield % |
|---|---|---|---|---|---|---|---|
| 882 | pyrrolidine | 2 | Cl | $C_{14}H_{22}Cl_2N_2O_4S$ | 385 | 209 | 83 |
| 883 | piperidine | 2 | Cl | $C_{15}H_{24}Cl_2N_2O_4S$ | 399 | 220 | 83 |
| 884 | morpholine | 2 | Cl | $C_{14}H_{22}Cl_2N_2O_5S$ | 401 | 232 | 82 |
| 888 | piperidine | 3 | Cl | $C_{16}H_{26}Cl_2N_2O_4S$ | 413 | 191 | 85 |
| 889 | morpholine | 3 | Cl | $C_{15}H_{24}Cl_2N_2O_5S$ | 415 | 212 | 61 |
| 899 | pyrrolidine | 2 | OCH₃ | $C_{15}H_{25}ClN_2O_5S$ | 380,5 | 186 | 89 |
| 926 | pyrrolidine | 2 | Br | $C_{14}H_{22}BrClN_2O_4S$ | 429,75 | 226 | 64 |
| 927 | piperidine | 2 | Br | $C_{15}H_{24}BrClN_2O_4S$ | 443,78 | 204 | 71 |
| 928 | morpholine | 2 | Br | $C_{14}H_{22}BrClN_2O_5S$ | 445,75 | 246 | 71 |
| 932 | piperidine | 3 | Br | $C_{16}H_{26}BrClN_2O_4S$ | 457,80 | 200 | 60 |
| 933 | morpholine | 3 | Br | HCl, $C_{15}H_{24}BrClN_2O_5S$ base $C_{14}H_{23}BrN_2O_5S$ | 459,77 | 237 127 | 72 |

TABLE I-continued
COMPOUNDS OF FORMULA

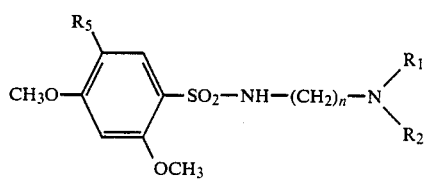

| Product n° | N(R1)(R2) | n | R5 | Formula of compound in form of hydrochloride | Molecular weight | Melting point of hydrochloride | Yield % |
|---|---|---|---|---|---|---|---|
| 957 | azetidinyl (N-ring) | 2 | $SO_2CH_3$ | $C_{15}H_{25}N_2O_6S_2Cl$ | 428,935 | 232 | 62 |
| 959 | morpholino | 2 | $SO_2CH_3$ | $C_{15}H_{25}N_2O_7S_2Cl$ | 444,932 | 246 | 66 |
| 980 | $N(C_2H_5)_2$ | 2 | $SO_2C_2H_5$ | $C_{16}H_{29}ClN_2O_6S_2$ | 444,978 | 242 | 71 |
| 988 | morpholino | 3 | $SO_2C_2H_5$ | $C_{17}H_{29}ClN_2O_7S_2$ | 472,986 | 204 | 70 |
| 1 095 | $N(C_2H_5)_2$ | 2 | $SO_2-nC_3H_7$ | $C_{17}H_{31}ClN_2O_6S_2$ | 459 | 224 | 91 |
| 1 098 | morpholino | 2 | $SO_2-nC_3H_7$ | $C_{17}H_{29}ClN_2O_7S_2$ | 472,99 | 186 | 83 |
| 1 104 | $N(CH_3)_2$ | 2 | $SO_2-iC_3H_7$ | HCl, $C_{15}H_{27}ClN_2O_6S_2$ | 430,95 | 217 | 71 |
| 1 109 | azetidinyl (N-ring) | 2 | $SO_2-iC_3H_7$ | $C_{17}H_{29}ClN_2O_6S_2$ | 456,99 | 222 | 77 |
| 1 113 | 2-methylpiperidino | 3 | $SO_2-iC_3H_7$ | $C_{20}H_{35}ClN_2O_6S_2$ | 499,07 | 200 | 65 |

The new benzenesulfonamides prepared from the sulfochlorides according to the invention, as well as their physiologically acceptable organic or inorganic salts have remarkable pharmacological properties.

The compounds prepared from the sulfochlorides according to the invention exert a control effect on the central nervous system and particularly a psychomodulator effect. They can act particularly as antidepressant agent or as tranquilizing anxiolytic agents.

The activity of these compounds prepared from the sulfochlorides is reinforced by the lipophile nature of the molecule, due to the presence of an alkoxy group on the aromatic nucleus at the 4 position.

The compounds prepared from the sulfochlorides according to the invention are distinguished also by the fact that they potentiate pentobarbital sleep, that they have little or no affinity for the dopaminergic sites customarily recognized as associated with certain undesirable effects (galactorhea, amenorrhea, extrapyramidal syndromes) and that they are devoid of toxicity.

Their therapeutic index is compatible with their use as a medicine.

The compounds prepared from the sulfochlorides according to the invention are advantageously introduced as active principles in the treatment of disorders with depressive, anxiety components causing in particular psychosomatic disturbances.

The compounds prepared from the sulfochlorides according to the invention are for this purpose associated with the traditional excipients and adjuvants, particularly those used for the preparation of tablets, powders, capsules, drinkable ampoules and injectable solutions.

The administration of the medicaments containing the compounds prepared from the sulfochlorides according to the invention, is preferably effected orally, parenterally, rectally or topically, and the doses of active compound administered are preferably comprised between 10 and 700 mg and particularly between 50 and 500 mg/day.

By way of example, different tests for the establishment of the pharmacological properties of the compounds prepared for the sulfochlorides according to the invention, are reported below.

TESTS RELATING TO THE STUDY OF THE INTERACTIONS OF THE MEDICAMENTS ACCORDING TO THE INVENTION WITH PENTOBARBITAL

The tests were carried out on Swiss Iops mice, of the male sex, weighing from 20 to 24 g, obtained from the Le Genest breeding center.

The animals were acclimatized at least 8 days in the animal section of the laboratory before the tests.

The batches were of 10 mice per test and per product.

As reference products, to carry out control tests, the three following substances were used:

N-[(1-ethyl 2-pyrrolidinyl)methyl]2-methoxy 5-sulfamoyl benzamide known under the name sulpiride;

N-[(1-ethyl 2-pyrrolidinyl)methyl]2-methoxy 5-ethylsulfonyl benzamide known under the name sultopride;

N-(2-diethylamino ethyl)2-methoxy methyl 5-sulfonyl benzmide known under the same tiapride.

The compounds obtained from the sulfochlorides according to the invention and the reference substances were administered in aqueous suspension in ordinary water with 3% of gum arabic orally (interaction tests with barbiturates).

The pharmacological reagent, namely pentobarbital, was administered in solution in an isotonic NaCl solution.

The volumes administered were 0.5 ml of a solution at 1.6 g/l per 20 g of body weight intraperitoneally (40 mg/kg).

To carry out these tests, the compounds obtained from the sulfochlorides according to the invention or the reference products (namely sulpiride, sultopride or tiapride) were administered to batches of 10 male SWISS mice orally in the dose of 200 mg/kg. 60 minutes after ingestion of the compounds obtained from the sulfochlorides according to the invention of of the reference products, the pentobarbital was administered to the animals in sodium form such as that marketed under the name Nembutal.

Then measurement was made of:
drowsiness time,
sleeping time, and the percentage of variations in addition to or less than the sleeping time was determined. The results of these tests are shown in the following Table II.

TABLE II

| Product n° | Sleeping time (pentobarbital) mn | Variation % |
|---|---|---|
| 882 | 176 ± 21 | +144.4 |
| 883 | 176 ± 12 | +147.9 |
| 884 | 150 ± 24 | +111.3 |
| 888 | 140 ± 20 | +97.2 |
| 889 | 156 ± 15 | +119.7 |
| 899 | | +23.1 |
| 926 | 168 ± 30 | +133.3 |
| 927 | 169 ± 26 | +134.7 |
| 928 | 165 ± 24 | +129.2 |
| 932 | 142 ± 15 | +97.2 |
| 933 | 180 ± 32 | +150.0 |
| 957 | | +26.8 |
| 959 | | +41.7 |
| 980 | | +21.1 |
| 988 | | +9.9 |

It is interesting to note that the combination of substitution of the 2,4 positions by alkoxy groups and the substitution of the 5 position confers on the novel benzenesulfonamides trisubstituted at the 2,4,5 position particularly effective biological properties; it seems that this effectiveness must be attributed to the trisubstituted structure of the phenyl portion of these benzenesulfonamides, which trisubstituted structure is to be found in the sulfochlorides according to the invention.

Study of the results obtained shows that the benzenesulfonamides obtained from the sulfochlorides according to the invention are psychomodulators. Those for which the percentage of the variation of the sleep time is higher than +50% are very distinct potentiators of pentobarbital sleep and consequently can be used as tranquilizers or anxioloytic agents.

The compounds obtained from the sulfochlorides according to the invention for which the percentage of the variation of the sleep time varies from about 0% to about 50% are potentiators close to reference compounds sultopride and tiapride used.

The compounds obtained from the sulfochlorides according to the invention for which the percentage in the variation of the sleep time is less than 0% are antagonists and can be used as antidepressant agents.

It is noted that the sulpiride used as a reference product shows itself rather to be as much potentiator, as antagonist which introduces its double character as neuroleptic and antidepressant agent.

I claim:

1. A sulfohalide of the formula:

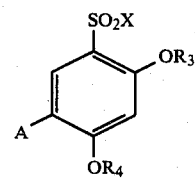

wherein:
X is chlorine or bromine;

$R_3$ and $R_4$ is alkyl from 1 to 4 carbon atoms;

A is Cl, Br, $CF_3$, $NO_2$ or alkyl sulfonyl having from 1 to 4 carbons;

provided that when X is Cl and $R_3$ and $R_4$ both are $CH_3$, A is different from Cl.

2. A sulfohalide of the formula:

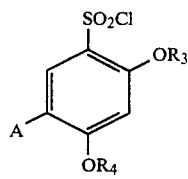

wherein:

$R_3$ and $R_4$ are alkyl having from 1 to 4 carbon atoms;

A is Cl, Br, $CF_3$, $NO_2$ or alkyl sulfonyl having from 1 to 4 carbons;

provided that when $R_3$ and $R_4$ both are $CH_3$, A is different from Cl.

3. A sulfohalide of the formula:

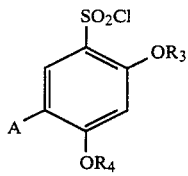

wherein $R_3$ and $R_4$ represent alkyl groups having 2 to 4 carbon atoms, and A represents Cl, Br, $CF_3$ or $NO_2$.

4. A sulfohalide of the formula:

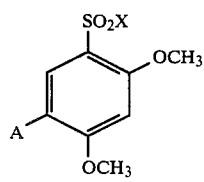

wherein

X is chlorine or bromine;

A is Cl, Br, $CF_3$, $NO_2$ or alkyl sulfonyl having from 1 to 4 carbons;

provided that when X is Cl, A is different from Cl.

5. A sulfohalide of the formula:

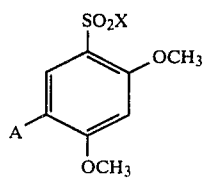

wherein X represents Br or Cl, and A represents Br, $CF_3$, or $NO_2$.

6. The sulfohalide of claim 5 wherein X is Cl.

7. The sulfohalide of claim 6 wherein A is Br or $CF_3$.

8. A sulfohalide of the formula:

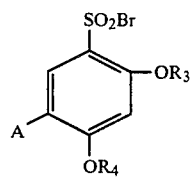

wherein $R_3$ and $R_4$ is alkyl having from 1 to 4 carbon atoms

A is Cl, Br, $CF_3$, $NO_2$, alkoxy having from 1 to 4 carbon atoms or alkyl sulfonyl having from 1 to 4 carbons.

9. A sulfohalide of the formula

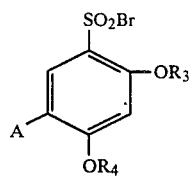

wherein $R_3$ and $R_4$ represent alkyl groups having from 1 to 4 carbon atoms, and A represents Cl, Br, $CF_3$, $NO_2$ or an alkoxy group having from 1 to 4 carbon atoms.

10. A sulfohalide of the formula:

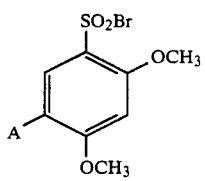

wherein

A is Cl, Br, $CF_3$, $NO_2$, alkoxy having from 1 to 4 carbon atoms or alkyl sulfonyl having from 1 to 4 carbons.

* * * * *